(12) United States Patent
Krenkel et al.

(10) Patent No.: US 6,666,869 B2
(45) Date of Patent: Dec. 23, 2003

(54) ENDO-DISTRACTOR

(75) Inventors: Christian Krenkel, Salzburg (AT); Georg Lixl, Oberndorf (AT)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/230,074

(22) Filed: Aug. 29, 2002

(65) Prior Publication Data

US 2003/0055433 A1 Mar. 20, 2003

Related U.S. Application Data

(63) Continuation of application No. PCT/CH00/00117, filed on Feb. 29, 2000.

(51) Int. Cl.$^7$ .............................................. A61B 17/58
(52) U.S. Cl. ...................................................... 606/73
(58) Field of Search .............................. 606/72, 73, 86, 606/90, 105, 63, 65; 433/172–176

(56) References Cited

U.S. PATENT DOCUMENTS

| | | | | |
|---|---|---|---|---|
| 4,187,841 A | * | 2/1980 | Knutson ...................... | 606/105 |
| 4,708,132 A | * | 11/1987 | Silvestrini .................... | 606/86 |
| 5,082,445 A | * | 1/1992 | Singer ........................ | 433/169 |
| 5,141,513 A | * | 8/1992 | Fortune et al. ............... | 606/96 |
| 5,217,462 A | * | 6/1993 | Asnis et al. .................. | 606/73 |
| 5,360,431 A | * | 11/1994 | Puno et al. ................... | 606/73 |
| 5,571,016 A | * | 11/1996 | Ingber et al. ................ | 433/173 |
| 5,743,912 A | * | 4/1998 | Lahille et al. ................ | 606/73 |
| 5,899,940 A | * | 5/1999 | Carchidi et al. .............. | 606/73 |
| 5,964,767 A | * | 10/1999 | Tapia et al. ................... | 606/73 |
| 5,968,044 A | * | 10/1999 | Nicholson et al. ............ | 606/72 |
| 5,997,541 A | * | 12/1999 | Schenk ........................ | 606/73 |
| 6,306,143 B1 | * | 10/2001 | Kvarnstrom et al. ........ | 606/105 |

* cited by examiner

*Primary Examiner*—David O. Reip
*Assistant Examiner*—Jessica R Baxter
(74) *Attorney, Agent, or Firm*—Pennie & Edmonds LLP

(57) ABSTRACT

The invention relates to a device for the distraction of bones or bone segments. The device comprises an anchoring screw having a longitudinal axis, a screw tip, a screw end with means for rotatably driving the anchoring screw, a threaded shank which adjoins the screw tip and has a screw thread, and a screw shank adjoining the screw end; and a distraction sleeve axially displaceable on the screw shank including a rear end, a front end, a through-bore extending coaxially therebetween, an external thread adjoining the front end, and a coupler portion formed in the rear end for receiving a driving tool. The anchoring screw comprises a collar positioned between the threaded shank and the screw shank that radially projects at least from the screw shank and which serves as an axial stop for the front end of the distraction sleeve when the distraction sleeve is positioned over the screw shank. The through-bore has a boring section with an enlarged cross-section which adjoins the rear end provided with a lateral surface and a seal ring coaxially arranged between the lateral surface and the screw shank.

12 Claims, 4 Drawing Sheets

ENDO-DISTRACTOR

CROSS-REFERENCE TO RELATED APPLICATIONS

This application is a continuation of the U.S. national stage designation of copending International Patent Application PCT/CH00/00117, filed Feb. 29, 2000, the entire content of which is expressly incorporated herein by reference thereto.

FIELD OF THE INVENTION

The present invention relates generally to an apparatus for the distraction of bone or bone segments.

BACKGROUND OF THE INVENTION

In modern surgical operative technique, external or also internal distractors are used to bring about a controlled displacement of bone fragments relative to one another. Endo-distractors are especially suitable for oral surgery, as they allow to minimize the disturbance of the patient during the distraction process which may often take several weeks.

Distractors are also used with toothless jaws in cases of advanced atrophy of the mandible. Apart from the cosmetic aspect, mandibular atrophy may also create difficulties for the implantation of a set of artificial teeth. The absence of the necessary bone substance may lead to a loosening of the implants or even to a fracture of the mandible. A pathological atrophy of the mandible is not only observed with old patients but may even occur with a 40-year-old patient, in which case the decision in favor of an operative intervention is greatly facilitated.

In order to rebuild the mandible, an osteotomy of the mandible is realized in a horizontal direction. Subsequently, the osteotomy gap is continuously increased. This distraction of the osteotomy gap is carried out at a rate on the order of about ½ mm per day. During the slowly advancing process of distraction, osseous tissue is formed in the osteotomy gap. After completion of the distraction, the osteotomy gap has to be maintained at the right distance for a certain period of time.

SUMMARY OF THE INVENTION

The present invention is directed to a device for the distraction of bones or bone segments comprising an anchoring screw having a longitudinal axis, a threaded shank, a screw shank, and a screw end provided with means for rotatably driving the anchoring screw, as well as a distraction sleeve axially displaceable along the screw shaft extending coaxially along the longitudinal axis and is provided with a rear end, a front end, a circular cylindrical, through-bore, an external screw thread adjoining the front end, and a coupling means formed on the rear end for receiving a driving tool. In addition, the anchoring screw comprises a collar located between the threaded shank and the non-threaded shank and projecting radially at least over the non-threaded shank so as to serve as an axial stop for the front end of the distraction sleeve that is slid over the screw shank. The through-bore comprises a boring section with an enlarged cross-section in which a seal ring is coaxially arranged between the lateral surface of the boring section and the screw shank.

In one embodiment of the device, the collar is shaped in the form of a cone which leads to the screw shaft. Thus, the contact surface between said cone and the front end of the distraction sleeve is minimized, which has the advantageous result that in spite of the axial load existing between the anchoring screw and the distraction sleeve, the anchoring screw remains easily rotatable about the longitudinal axis. Alternatively, the transition segment may also be spherically convex.

The device according to the invention comprises in addition, a cover screw which may be screwed into a bore formed on the screw end and provided with an internal screw thread. The cover screw forms the mechanical seal of the distractor in the oral cavity and, in addition, secures the anchoring screw in its position relative to the distraction sleeve.

In another embodiment, the collar comprises a spherically convex, tapered portion which leads to the screw shank. Also, the boring section can have an inner cone which leads to the through-bore. In another embodiment, the screw thread may be self-tapping, or the screw thread can have an asymmetrical thread profile. Also, the screw thread may include flanks directed towards the screw tip that form an angle of between 80 and 90 degrees with respect to the longitudinal axis.

Also, the external thread may have an asymmetrical thread profile, and the external thread may include flanks directed towards the rear end that form an angle of between 80 and 90 degrees with respect to the longitudinal axis, and the thread profile of the external thread may have flattened, threaded tips. In one embodiment, the means for rotatably driving the anchoring screw do not radially protrude from the screw shank.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
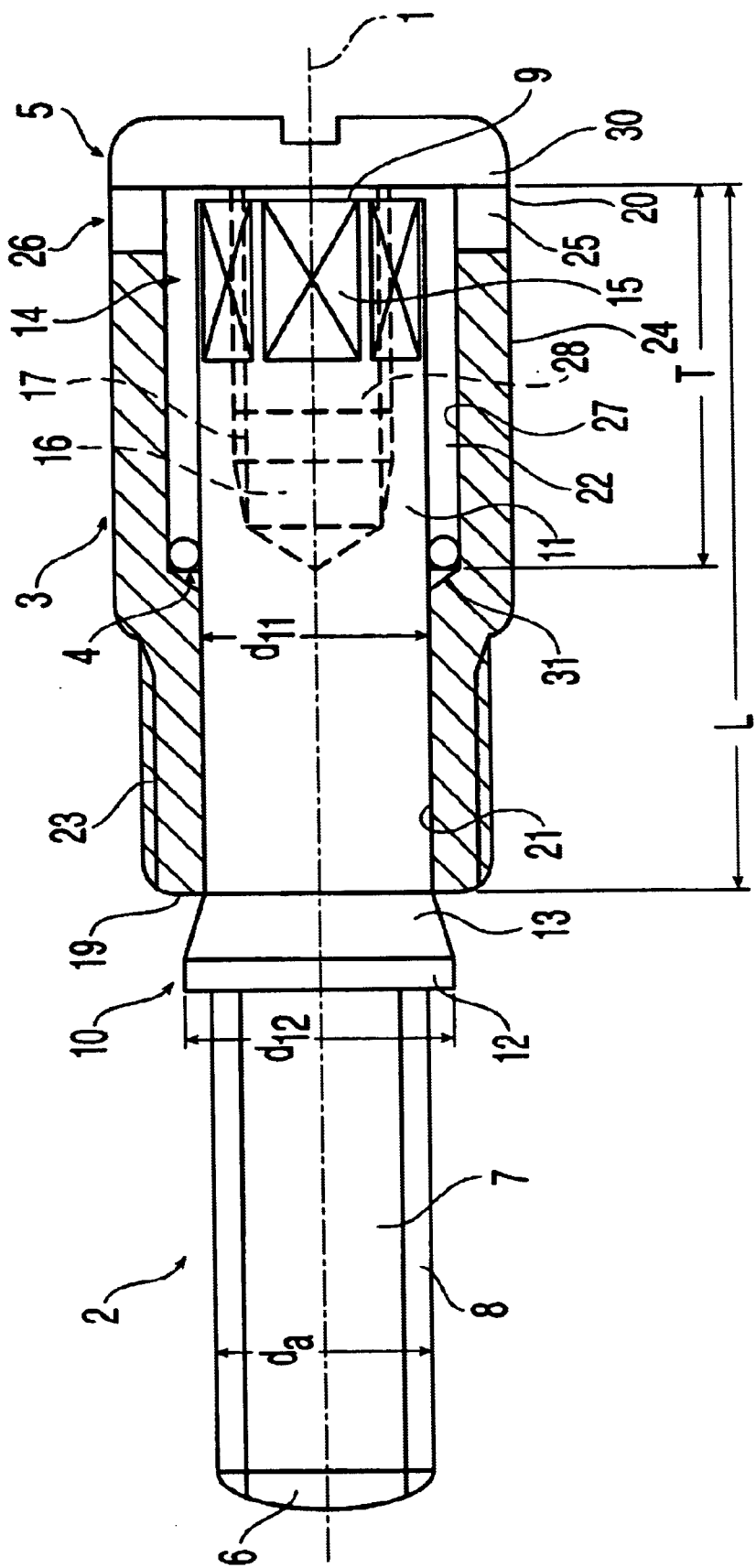
FIG. 1 is a longitudinal section of the preferred embodiment of the device according to one embodiment of the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

FIG. 1 shows one preferred embodiment of the distraction device according to the invention. The distraction device comprises an anchoring screw 2 having a longitudinal axis 1 as well as a distraction sleeve 3 extending coaxially along longitudinal axis 1, a seal ring 4, and a cover screw 5. The anchoring screw 2 is circular cylindrical and includes a threaded shank 7 which adjoins a rounded screw tip 6 and has a screw thread 8 that extends over approximately half of the anchoring screw 2 and is provided with an outside diameter $d_a$. Threaded shank 7 is adjoined respectively by a collar 10 and a circular cylindrical screw shank 11 with a diameter $d_{11}$ which are axially arranged in the mentioned order in the direction of the screw end 9. The screw thread 8 is asymmetrically shaped, forming an angle of 87 degrees between the flanks of the screw thread directed towards the screw tip 6 and the longitudinal axis 1. Facing the threaded shank 7, the collar 10 has a circular cylindrical section 12 with a diameter $d_{12}$. Diameter $d_{12}$ is superior to outside diameter $d_a$ and superior to diameter $d_{11}$ of the screw shank 11. Facing the screw shank 11, collar 10 comprises a transition segment or cone 13 which leads in a conically tapered manner from section 12 to screw shank 11. Depending on the type of seal ring 4 used, the transition segment between the boring segment with enlarged cross-section and the through-bore of the distraction sleeve may be shaped either in the form of a plan surface or of an inner cone leading to the through-bore. Thus, a suitable axial contact surface for the seal ring 4 may be obtained.

In one embodiment, the external screw thread formed on the distraction sleeve is preferably realized as a left-hand thread. In one embodiment, the screw thread is in the form of a self-tapping screw thread which may be provided with one or several cutting grooves. The outside diameter of the screw thread may be in a range of between 2.2 mm and 3.5 mm, but is preferably about 2.7 mm. The thread profile is preferably asymmetrical, and the flanks of the screw thread directed towards the screw tip preferably forming an angle of between 80 and 90 degrees relative to the longitudinal axis. Thus, the pressure load may be transmitted in a substantially axial manner to the cancellous bone. The diameter of the screw shank may be in a range of between 1.8 mm and 2.5 mm, but is preferably about 2.2 mm. The means for driving the anchoring screw preferably does not radially project from the screw shank and may, for example, consist of surfaces evenly arranged in a polygonal pattern on the periphery of the screw shank so as to form preferably a square or a hexagon.

Means 14 for driving the anchoring screw 2 are arranged on screw shank 11 in the area of screw end 9. In one embodiment, driving means 14 are in the form of a hexagon consisting of six surfaces 15 regularly arranged about the periphery of the screw shank 11. Screw end 9 is provided with a bore 16 extending coaxially to the longitudinal axis 1 and provided with an internal screw thread 17.

The distraction sleeve 3 is shaped in the form of a hollow cylinder extending coaxially along longitudinal axis 1 and has a front end 19, a rear end 20, and a length L extending parallel to longitudinal axis 1. The distraction sleeve 3 comprises an external screw thread 23 beginning on the front end 19 and extending over half of the length L. The sleeve segment 24 that adjoins the rear end 20 has an enlarged diameter and is provided with four slots 25 arranged on the rear end 20 and extending orthogonally relative to one another so as to serve as a coupling means 26 for receiving a screwing-in or driving tool. A continuous boring or through-bore 21 extends coaxially to the longitudinal axis 1 and is of circular cylindrical shape and has a diameter that permits the distraction sleeve 3 to be axially displaced along the screw shank 11. Beginning from the rear end 20, through-bore 21 has a boring section 22 with an enlarged cross-section which penetrates to a depth T, the boring section 22 conically leading to the through-bore 21 with half a cone angle of 60 degrees and the depth T being dimensioned in such a way that the boring section 22 does not extend over the entire sleeve segment 24. The distraction sleeve 3 may be slid over the screw shank 11 from the screw end 9 until its front end 19 abuts on the cone 13, the distraction sleeve 3 remaining freely rotatable on the screw shank 11 about the longitudinal axis 1 and the rear end 20 projecting over the screw end 9.

The external screw thread formed in the distraction sleeve may equally be advantageously provided with an asymmetrical thread profile, the flanks of the screw thread directed towards the rear end forming an angle of between 80 and 90 degrees relative to the longitudinal axis. Here again, a substantially axial transmission of the pressure load to the bone may be obtained.

Between lateral surface 27 of the boring section 22 and the screw shank 11, seal ring 4 is arranged which ensures a tight sealing between the oral cavity and the mandible.

The distraction sleeve has many functions, including but not limited to: abutment for lifting the upper osteotomy segment; gingiva former in view of the implant to be subsequently inserted; provide protected access to the internal screw, permitting to turn said screw; providing sealing possibility by means of kneaded wax due to the countersinking of the internal screw (a difference in level of 0.5 mm between the upper edge of the distraction sleeve and the end of the anchoring screw may be provided to lodge the bead of kneaded wax); and as a sleeve for receiving O-rings ensuring a tight sealing of the bone against saliva and bacteria.

In addition, the distraction device comprises a cover screw 5 which includes a threaded portion 28 which may be screwed into the internal screw thread 17 formed in the screw end 9 until the screw head 30 abuts on the rear end 20 of the distraction sleeve 3. The cover screw seals the dead space of the distraction sleeve, it has a function similar to that of a gingiva former and offers some degree of support for a temporary prosthesis.

The distractor device may be used for many applications, including but not limited to the distraction of the alveolar processes of the mandible extending over a large surface, distraction of the alveolar processes of the maxilla extending over a large surface, local distraction of the alveolar crest, cheekbone distraction, chin augmentation distraction, augmentation distraction of the border of the mandible, distraction of the mandibular neck, bone transport in cases of deficiencies in the ramus of the mandible in combination with a functionally dynamic bridging plate, as well as in other osseous parts of the body, such as finger distractions.

The distraction device may be used as an endo-distraction implant in at least the following two basic modes of application, each mode of application showing two different types which may be mutually combined:

In one mode of application (mode A), the distraction device may be used when the osteotomy fragment is situated distally relative to the skin or the mucous membrane and provided with the bone thread for receiving the anchoring screw forms the stationary part, whereas the osteotomy fragment facing the skin or the mucous membrane and lodging the distraction sleeve forms the mobile part that is displaced relative to the stationary, principal fragment during the distraction treatment. This mode of application may be used, for example, for distractions of the alveolar processes of the maxilla and the mandible extending over a large surface, for local distractions of the alveolar crest, distractions of the cheekbone, distractions of the mandibular neck, and for other osseous regions of the body, such as finger distractions.

In another mode of application (Mode B), the device is used as a distraction device in which the osteotomy fragment situated distally relative to the skin or the mucous membrane and provided with the bone thread for receiving the anchoring screw forms the mobile part, whereas the osteotomy fragment facing the skin or the mucous membrane and lodging the distraction sleeve forms the stationary part which pushes away the mobile bone part with the bone thread during the distraction treatment. This mode of application is used, for example, for chin augmentation distractions, augmentation distractions of the border of the mandible, bone transport in cases of deficiencies in the ramus of the mandible in combination with a functionally dynamic bridging plate, and for other osseous parts of the body.

In this regard, the distractor device may be used as an endo-distraction implant in which the distraction sleeve including a stop for the anchoring screw is an implant screwed into the bone and thus rigidly connected to the osteotomy segment. This implant type may be used, for example, for distractions of the alveolar processes of the maxilla and the mandible extending over a large surface and for local distractions of the alveolar processes.

Also, the distractor device may be used as an endo-distraction implant in which the abutment including a stop for the anchoring screw is stabilized straight or at various different angles relative to the bone, as required, by means of small miniature plates using specially designed screws. This implant type may be used, for example, for cheekbone distractions, for chin augmentation distractions, augmentation distractions of the border of the mandible, distractions of the mandibular neck, and bone transport in cases of deficiencies in the ramus of the mandible in combination with a functionally dynamic bridging plate.

Figure 2:
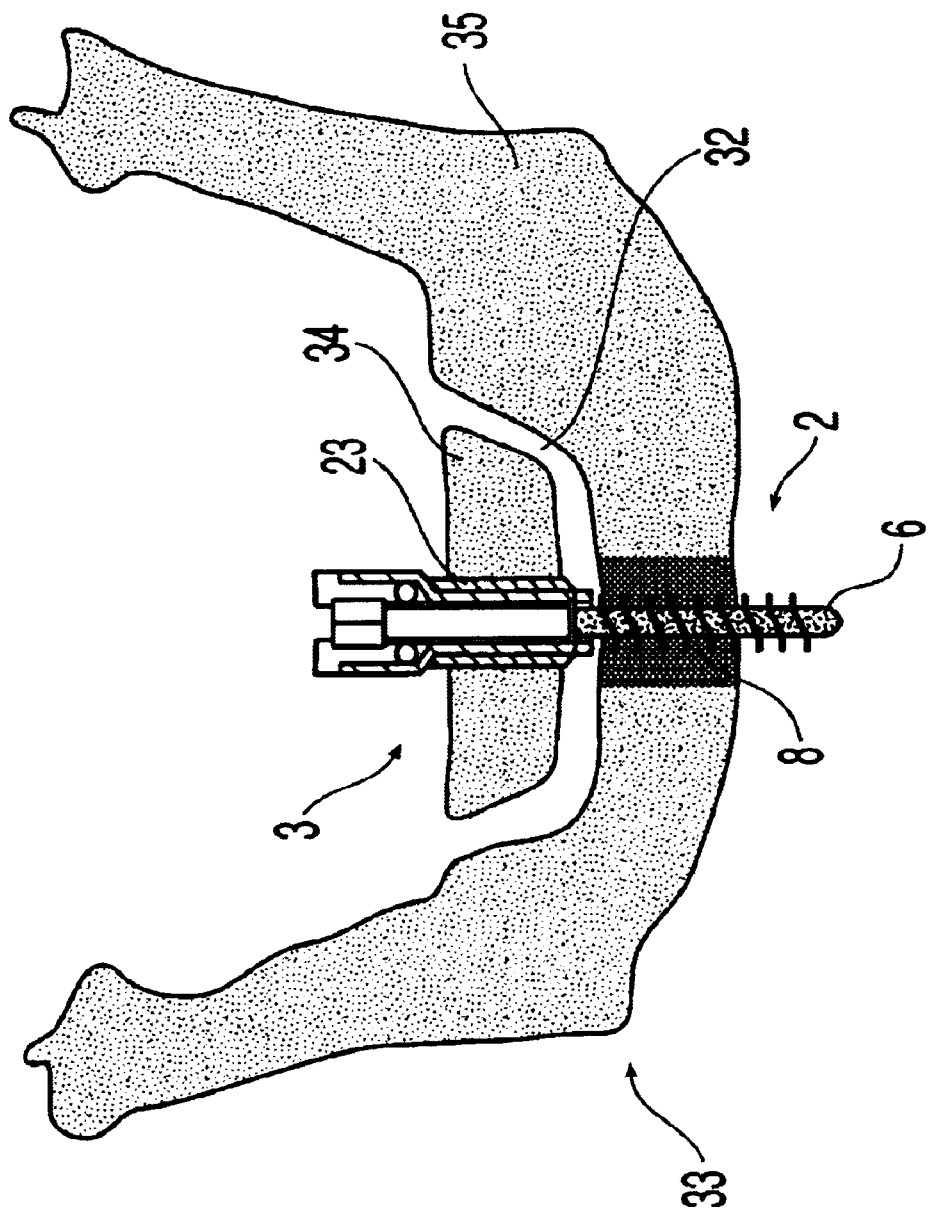
FIG. 2 is a sectional view of a mandible at the beginning of the distraction process, including a device according to the invention inserted therein.
Figure 3:
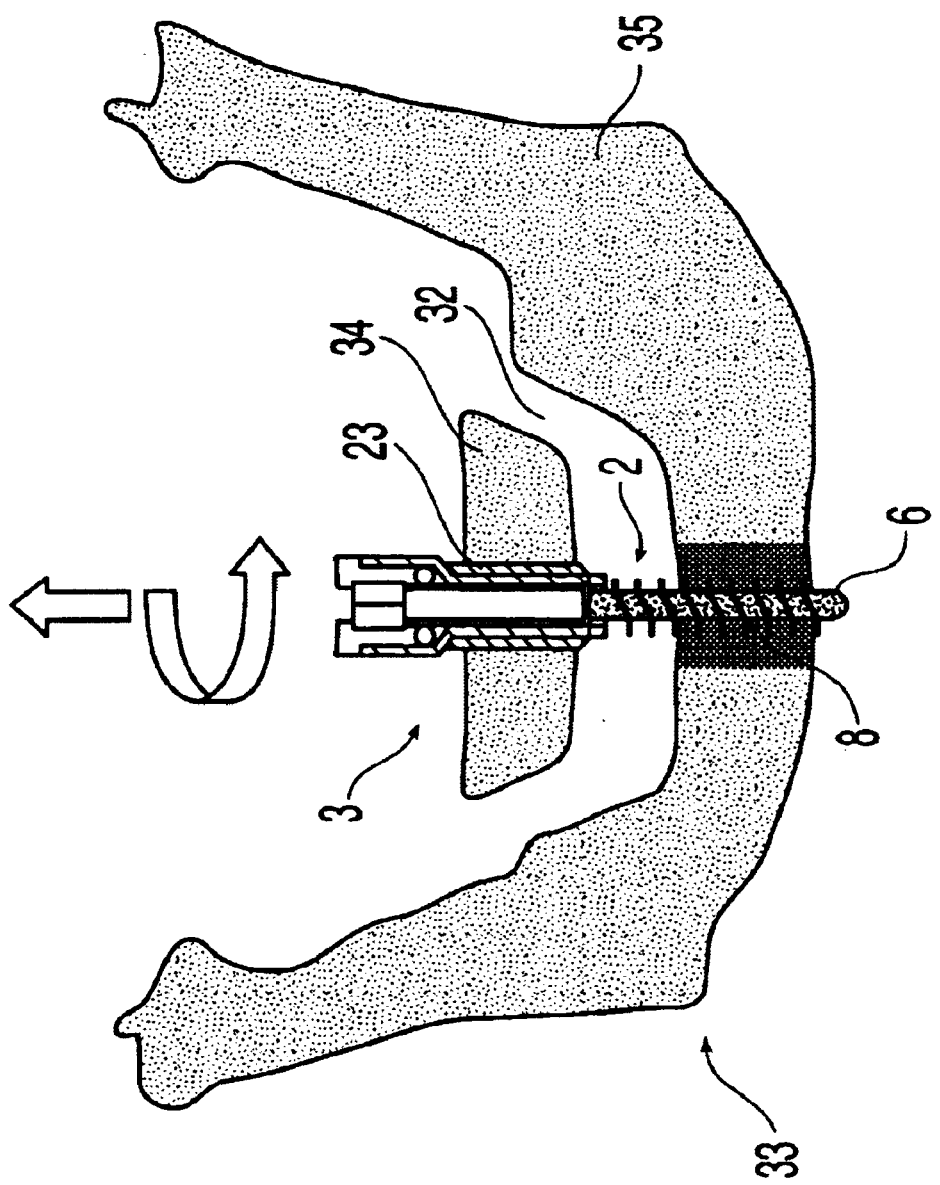
FIG. 3 is a sectional view of a mandible during the distraction process, including a device ac cording to the invention inserted therein.

FIGS. 2 and 3 illustrate a distraction process through the example of a mandible 33 having undergone osteotomy and presenting an osteotomy gap 32. The drawings show in particular a distraction process according to Mode A in which the alveolar process is displaced in the cranial direction. As described above, the anchoring screws 2 of the endo-distractors are passed through the cranial bone segment 34 and through the osteotomy gap 32 and are then inserted into the caudal bone segment 35. The anchoring screws 2 are screwed into the caudal bone segment 35 until their threaded tips 6 protrude from the opposite side thereof. The excessive length corresponds to the amount of distraction to be obtained for the osteotomy gap. The distraction sleeves 3 are inserted into the cranial bone segment 34 and prevent the anchoring screws 2 from moving in the cranial direction. As the anchoring screw 2 is screwed backwards, the cranial bone segment 34 is lifted in the cranial direction by the action of the distraction sleeve 3, while the caudal bone segment 35 remains stationary.

Figure 4:
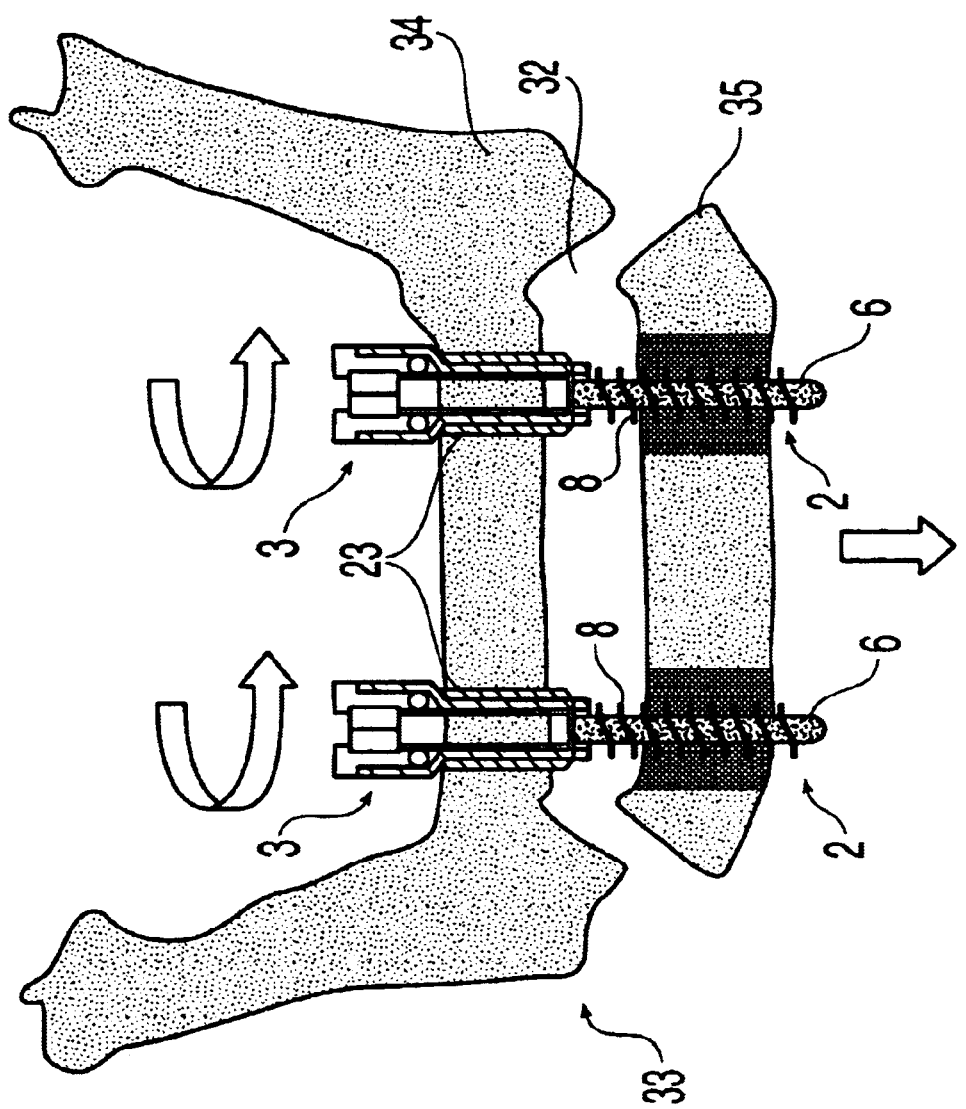
FIG. 4 is a sectional view of a mandible during the distraction process, including two devices according to the invention inserted therein.

FIG. 4 illustrates the distraction process according to Mode B through the example of a mandible 33 that has undergone osteotomy. In this example the distraction results in a displacement of the chin in the caudal direction.

One skilled in the art may appreciate that when the distractor device is used, the distraction force is preferably applied in the center of gravity of the distraction so that the distraction device is preferably exclusively exposed to axial pressure and not to any flexural strain, which facilitates an endo-distraction device having small dimensions. Also, the distraction occurring subsequent to an osteotomy may begin horizontally offset, representing at the same time a horizontal displacement osteotomy, and the offset may be carried out in a controlled manner. The distraction following the osteotomy may also be carried out in different directions, depending on the angle relative to the osteotomy plane selected for the bore designed to receive the endo-distractor, which allows for corrective measures in cases of a defective relation of the crests of the maxilla and the mandible as a preparation for a prosthetic appliance to be placed subsequently.

Furthermore, it should be recognized that the distraction sleeve, together with its cover screw, may serve to stabilize a temporary prosthesis during the retention period of several months and may assume a function comparable to that of a dental implant. In this regard, putting load on the endo-distractor and, as a consequence, on the freshly distracted bone at an early stage provides a great deal of functional stimuli and thus may lead to an accelerated bone formation in the distraction area. Also, since the screw thread of the distraction sleeve is counterrotating it is secured against being screwed off in the course of the distraction. After the removal of the distraction sleeve, the left-hand thread of the latter leaves behind a left-hand thread formed in the bone. This thread, together with the right-hand thread formed in the lower bone segment, simultaneously has the function of a pilot bore for the implant to be placed in the course of the same surgical intervention once the endo-distractor has been removed. These threaded bores therefore represent at the same time the pilot bores for receiving the dental implant to be subsequently inserted. The osseous left-hand thread of the hollow implant, after the cutting of a right-hand thread for a dental implant, results in a reliable, new bone thread providing a good primary seat for the dental implant. The two counterrotating threads cross at different positions, depending on the difference in their respective thread pitches. All types of dental implants can be used, no matter what kind of screw thread they may have, and the surgeon is not limited to a particular type of implant to be used for the prosthetic treatment.

With the aid of the distraction device, the following exemplary surgical technique for the distraction of the mandible may be realized: the mandible is split horizontally using accesses that avoid excessive soft-tissue damage (osteotomy). Depending on the situation, any number of distractor devices or endo-distractors may be used. The anchoring screws of the endo-distractors are passed through the cranial bone segment and the osteotomy gap and are then inserted into the caudal bone segment. The anchoring screws are screwed into the caudal bone segment until their threaded tips protrude from the opposite side thereof. The excessive length corresponds to the amount of distraction to be obtained for the osteotomy gap. The distraction sleeves are inserted into the cranial bone segment and prevent the anchoring screws from moving in the cranial direction.

The actual distraction process takes place during several days or weeks and in most cases is carried out by the patient himself. The patient turns back the anchoring screw by about ½ mm per day. As the distraction sleeve prevents the anchoring screw from being screwed out in the cranial direction, the cranial bone segment is lifted in the cranial direction by means of the distraction sleeve. Advantageously, this surgical technique may be realized with relatively unsophisticated technical equipment and the implants have a small volume.

Also, the distractor device allows vertical distraction of the alveolar processes of the maxilla and the mandible according to the Salzburg concept. It is of particular advantage if prior to the insertion of the implants the alveolar process can be "rebuilt" to its initial height. Preferably, the distance between the toothless alveolar processes of the maxilla and the mandible corresponds again to the height of natural teeth and the implant structures are low and therefore resistant. Also, preferably there are no recesses under the implants which are difficult to clean, and after completion of the distraction, the mandible has recovered its normal height and width and is capable of receiving long and stable implants, without running the risk of a spontaneous fracture.

As described above, the endo-distraction implant includes an abutment (with axial and radial function) for the anchoring screw and is integrated into a distraction sleeve inserted into the outer bone segment which does not need to have an internal screw thread and keeps the anchoring screw sealed tightly against bacteria and saliva by means of O-rings during the entire distraction and retention period. Also, the anchoring screw is inserted directly in a threaded bore tapped into the osseous substance of the bone segment situated on the opposite side of the osteotomy gap. A secure guidance and directional stability of the distraction process is preferably ensured by the threaded bore formed in the cortical bone. The distraction preferably occurs in the central part of the bone and preferably no part of the osteotomy line is covered on the outside by metal, which is an ideal condition for callus formation. The spare length of the anchoring screw corresponding to the extent of distraction required is preferably hidden deep in the soft tissues on the side opposite to the side on which the device is readjusted and, for this reason, preferably does not entail any negative effect on the patient.

One exemplary method of implantation involves first planning for the operation, for instance by observing surgical instructions concerning the distraction of the anterior mandible, providing anaesthesia, performing preparations, drafting and following a surgical drawing, electing a type of incision, measuring, and planning of the horizontal osteotomy. Next the horizontal osteotomy is performed and bores are drilled for receiving the implant and tapped. Tapping may be done for example by 2×tapping of a left-hand thread (4.0 mm) in the upper segment such as by means of a ratchet and with sufficient cooling the threads and until all the bone chips have been removed from the bone threads. Next the implants are screwed in, for example by using an adequate crown spanner and the ratchet, the two distraction sleeves are screwed completely into the two threads formed in the upper segment. In doing so, attention must be paid that the two O-rings placed within the distraction sleeve will not get lost, as they ensure that saliva, food residues, and germs are prevented from reaching the bone. The implant is then secured and osteoplasty may be performed followed by wound closure, an early postoperative period, a distraction period, a retention period, and finally, once the ossification has been completed satisfactorily insertion of the dental implants. For the prosthetic structures the following implant systems may be used: Ankylos implants; Bonefit implants; Frialit II implants; Brånemark implants, among others It will be appreciated that use of the longest implants available may be desirable, as long implants are apt to reach also the caudal osteotomy fragment, i.e. to bridge the distraction gap, which is necessary in order to counteract he tendency towards shrinking of the newly formed bone substance. In order to remove the inventive endo-distraction implants, a simple section of the crest of the mandible is performed, directly laying open the implant region. Positional records relating to the insertion of the implants are helpful for finding the location of the lateral implants at a safe distance from the mental nerve. First, the outer implants are inserted in the usual manner. Drilled bone chips occurring during the insertion of these implants are carefully harvested using the bone aspirator and temporarily stored in a cell nutrient solution. Subsequently, the distraction sleeves are screwed out clockwise (left-hand thread) using the crown spanner and the ratchet, after which the anchoring screws are screwed out anti-clockwise (right-hand thread) by means of their specific spanner. The following step consists in the bone preparation for the two mesial implants, great care being taken to temporarily store every bone fragment which can be harvested in a cell nutrient solution. In case of dehiscences occurring in the region between the inserted implants and the bone, these are carefully curetted and filled up with bone chips and bone meal. A semipermeable membrane placed over the implant prevents bone resorption and the ingrowth of connective tissue. After the mobilization of the mucous membranes, these are closed in two layers using slowly resorbable sutures. The sutures are removed two weeks after the implantation. A temporary prosthetic appliance can be made one week after the insertion of the implants at the earliest. Attention must be paid to ensure that the centric occlusion is absolutely correct and that the prostheses are repeatedly padded in short intervals.

It will be appreciated that when using the distractor device, the oral vestibule does not need to undergo a second surgical intervention which would otherwise be necessary to remove parts of the implant. In addition, the initially drilled bores can be used for the insertion of the final dental implant, which may be carried out under local anaesthesia in a simple manner easily acceptable for the patient. Also, the part of the endo-distraction implant to be worked on is preferably located at the same height relative to the surface of the skin or the mucous membrane, so that the temporary prostheses can be made at an early stage, and as a result, the number of implant parts may be reduced from at least three to no more than two. The distraction may be started in a controlled manner even with an offset relative to the osteotomy plane and by using different bore angles, the distraction may take place at various angles of inclination, depending on the specific requirements. The implant may be completely removed in a very easy manner by simply screwing out the distraction sleeve and the anchoring screw, and once the implant has been removed, the final dental implant may immediately be inserted using any of the commercially available implant systems, so that no further surgical intervention will be necessary.

It will also be appreciated that during the insertion process, no parts undergo mechanical deformation, so that any damage of an implant, which might otherwise occur during adaptation works even before the implant is used, can eliminated, and if in the course of a surgical intervention the application of a distraction device has failed, the distraction device may simply be inserted at another location.

If two distraction devices according to the invention are required in order to prevent twisting and to obtain a better distribution of the distraction forces, the two endo-distraction implants may be inserted parallel to each other at a wide or narrow distance. When inserted at a wide distance the daily distraction may be by an equal amount on both sides and may be achieved by turning on both devices in an exactly identical manner by means of a spanner (a mark on the spanner is necessary). Alternatively, the two devices may be inserted at a narrow distance to each other and be manipulated by means of an attachment which simultaneously rotates the two threaded rods by an identical angle of rotation in the same direction of rotation, thus causing a parallel distraction. An attachment of this type works with three serially interlocked gears the middle one of which being in engagement, by its axis, with the spanner, whereas the two outer gears drive the threaded rods by means of their axes.

One skilled in the art will further appreciate, that the left-hand thread of the hollow implant provides additional security while the right-hand thread of the threaded rod is used during the distraction. Should the hollow implant have become slightly loosened within the bone thread of the upper osteotomy segment, said implant is tightened again by the torque of the threaded rod as said threaded rod is screwed out. Generally, one and the same device may be used as an all-purpose device for the most diverse areas of application, and there is no necessity of further surgery for the removal of the device, as this intervention coincides with the insertion of the dental implants and, in addition, provides the bores required for the dental implants. Also, tight sealing of the bone against saliva and bacteria is provided on the distraction site. No unnaturally shaped parts are required, either in the oral cavity nor outside in the area of the face, so that no disfigurement occurs and the patient feels no embarrassment in pursuing such activities as eating, speaking, or mouth hygiene. Also, the endo-distractor according to the invention has the external shape of a single-tooth implant and is capable of providing support even during the retention period, similar to a tooth or a dental implant. As a result, the endo-distractor according to the invention is small but efficient as to the distraction length it allows, it acts in the centre of the bone in the structurally most favourable region, and the component parts are exclusively exposed to axial, compressive and tensile stress (absence of any lateral shear forces and flexural stresses that are typical of many other known devices), which ensures the greatest possible protection against fractures due to material fatigue.

What is claimed is:

1. A device for the distraction of bones or bone segments comprising:

an anchoring screw having a longitudinal axis, a screw tip, a screw end with means for rotatably driving the anchoring screw, a threaded shank which adjoins the screw tip and has a screw thread, and a screw shank adjoining the screw end; and a distraction sleeve axially displaceable on the screw shank including a rear end, a front end, a through-bore extending coaxially therebetween, an external thread adjoining the front end, and coupling means formed in the rear end for receiving a driving tool, wherein the anchoring screw comprises a collar positioned between the threaded shank and the screw shank that radially projects at least from the screw shank and which serves as an axial stop for the front end of the distraction sleeve when the distraction sleeve is positioned over the screw shank, the through-bore has a boring section with an enlarged cross-section which adjoins the rear end, said boring section being provided with a lateral surface; and a seal ring coaxially arranged between the lateral surface and the screw shank.

2. The device of claim 1, wherein the collar comprises a cone which leads to the screw shank.

3. The device of claim 1, wherein the collar comprises a spherically convex, tapered portion which leads to the screw shank.

4. The device of claim 3, wherein the boring section has an inner cone which leads to the through-bore.

5. The device of claim 4, further comprising a cover screw, and the screw end provided with a bore having an internal screw thread into which said cover screw may be screwed.

6. The device of claim 1, wherein the screw thread is self-tapping.

7. The device of claim 1, wherein the screw thread has an asymmetrical thread profile.

8. The device of claim 7, wherein the screw thread includes flanks directed towards the screw tip that form an angle of between 80 and 90 degrees with respect to the longitudinal axis.

9. The device of claim 8, wherein the external thread has an asymmetrical thread profile.

10. The device of claim 9, wherein the external thread includes flanks directed towards the rear end that form an angle of between 80 and 90 degrees with respect to the longitudinal axis.

11. The device of claim 10, wherein the thread profile of the external thread displays flattened, threaded tips.

12. The device of claim 11, wherein the means for rotatably driving the anchoring screw do not radially protrude from the screw shank.

* * * * *